(12) United States Patent
Hori

(10) Patent No.: US 7,527,595 B2
(45) Date of Patent: May 5, 2009

(54) PUMP PROVIDED WITH EXHAUST VALVE DEVICE AND HEMODYNAMOMETER INCORPORATING THE SAME

(75) Inventor: Kenichi Hori, Kanagawa (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 359 days.

(21) Appl. No.: 10/880,089

(22) Filed: Jun. 30, 2004

(65) Prior Publication Data

US 2005/0049513 A1    Mar. 3, 2005

(30) Foreign Application Priority Data

Aug. 29, 2003    (JP)   ............................ P2003-305925

(51) Int. Cl.
*A61B 5/02* (2006.01)
*F04B 23/00* (2006.01)

(52) U.S. Cl. ........................ 600/498; 417/440; 417/269; 417/283; 417/284; 417/407; 417/435; 251/264

(58) Field of Classification Search ................. 417/269, 417/307, 440, 283, 284, 207, 435; 251/264; 600/498
See application file for complete search history.

(56) References Cited

U.S. PATENT DOCUMENTS 5,220,925 A * 6/1993 Hishida ....................... 600/493
5,323,806 A * 6/1994 Watari et al. ................. 137/504
5,556,073 A * 9/1996 Wawro et al. .............. 251/129.11
5,921,951 A * 7/1999 Morris ........................ 604/6.11
6,592,339 B1 * 7/2003 Fukushima et al. .......... 417/269
6,843,643 B2 * 1/2005 Fukami et al. ............... 417/413.1

FOREIGN PATENT DOCUMENTS

| JP | 63-14809 | 4/1988 |
| JP | 2002-106471 | 4/2002 |

\* cited by examiner

*Primary Examiner*—Devon C Kramer
*Assistant Examiner*—Leonard J Weinstein
(74) *Attorney, Agent, or Firm*—Whitham Curtis Christofferson & Cook, P.C.

(57) ABSTRACT

A diaphragm is provided in a pump case so as to define a pump chamber communicated with an external member having an air chamber. The actuator is provided in the pump chamber. An exhaust valve is provided with a valve body, formed with a slit through which air the pump chamber is exhausted, and a screw member, screwed into a first wall of the pump case to adjust an opening amount of the slit by a screwed amount thereof, thereby adjusting an exhausting rate of the air in the pump chamber. The pump case is formed with a ventilation hole communicated with the pump chamber to allow the air exhausted from the slit to pass through.

2 Claims, 4 Drawing Sheets

PUMP PROVIDED WITH EXHAUST VALVE DEVICE AND HEMODYNAMOMETER INCORPORATING THE SAME

BACKGROUND OF THE INVENTION

The present invention relates to a compact pump provided with an exhaust valve device and a hemodynamometer employing the compact pump. Specifically, the invention relates to a compact pump which supplies air to an air chamber such as a cuff of the hemodynamometer to raise the pressure in the air chamber, and then releases the air to lower the pressure in the air chamber.

Such a compact pump is incorporated in, for example, an oscillometric hemodynamometer.

In the oscillometric hemodynamometer, a pump supplies air to a cuff wound around an upper am of a patient to compress an artery at a predetermined pressure to temporarily block a blood streams and the air is then released by a normal exhaust valve to gradually lower the pressure in the cuff. Incidentally, the variations of the internal pressure of the cuff and the vibration amplitude in accordance with the artery pulsations are processed by a microcomputer to measure the systolic blood pressure and the diastolic blood pressure. After the measurement processing, a rapid exhaust valve is operated to rapidly lower the internal pressure of the cuff.

Generally, it is preferable that the normal exhaust valve which is employed in the hemodynamometer has such a property that the pressure in the cuff is lowered at a constant speed of about 3 to 4 mmHg/sec., and the rapid exhaust valve has such a property that the pressure in the cuff is rapidly lowered FIG. 6 shows such a compact puma which is disclosed in Japanese Patent Publication No. 2002-106471A A compact pump 1 comprises: a pump body 2 which is driven by a motor (not shown); a normal exhaust valve 3 which exhausts an air through a slit at a constant speed (such an exhaust valve is disclosed in Japanese Utility Model Publication No. 63-14809Y, for example); a rapid exhaust valve 4 which is actuated by a plunger; and a flexible tube 5.

The normal exhaust valve 3 and the rapid exhaust valve 4 are separately provided from the pump body 2. The tube 5 interconnects an exhaust port 6 of the pump body 2, the normal exhaust valve 3 and the rapid exhaust valve 4, and is also connected to a cuff (not shown) which is wound around an upper arm of a patient. Inside the tube 5, there is formed an air passage 8 whir communicates respectively with a pump chamber 7 in the pump body 2, the normal exhaust valve 3, the rapid exhaust valve 4, and the cuff.

With the above configuration, when the pump body 2 is driven, exterior air is introduced into the pump chamber 7 and is then supplied to the cuff from the exhaust port 6 via the air passage 8 formed in the tube 5. When the internal pressure of the cuff reaches a predetermined pressure, the normal exhaust valve 3 is activated to exhaust air in the air passage 8. Incidentally, a larger amount of ail than the amount of the air exhausted by the normal exhaust valve 3 is introduced into the cuff from the pump chamber 7.

Here, since the driving of the pump body 2 is halted, the internal pressure of the cuff is gradually lowered by the normal exhaust valve 3. Incidentally, the variations of the internal pressure of the cuff and the vibration amplitude in accordance with the artery pulsations are processed by a microcomputer to measure the systolic blood pressure and the diastolic blood pressure. After the measurement processing, a rapid exhaust valve 4 is activated to rapidly lower the internal pressure of the cuff.

The normal exhaust valve 3 comprises an adjuster screw for adjusting the exhausting rate although it is not shown in FIG. 6. As disclosed in Japanese Utility Model Publication No. 63-14809Y, the adjuster screw is formed with a through hole extending along an axis of the screw. Such a screw is for an exclusive use, and has a higher price as compared with a common screw for general purpose, thereby increasing the component cost.

In addition, since the normal exhaust valve 3 and the rapid exhaust valve 4 are separately provided from the pump body 2, a large number of the components are required, the structure becomes complicated, thereby increasing the manufacturing cost.

Moreover, a piping structure of the tube 5 (the air passage 8) becomes complicated Since the tube 6 is exposed to the exterior of the pump body 2, the tube 5 might sometimes come into contact with other members and bent or crooked when the compact pump 1 is assembled, thereby lowering the workability of the assembling operation.

Further, a plunger for exclusive use is adopted as an actuator for the rapid exhaust valve 4, thereby increasing the component cost.

SUMMARY OF THE INVENTION

It is therefore an object of the invention to provide a pump provided with an exhaust valve device which is capable of decreasing the component cost, simplifying and downsizing the pump structure, and improving the facility to attach the pump to other equipment such as a hemodynamometer.

In order to achieve the above object, according to the invention, there is provided a pump, comprising:
 a pump case;
 a diaphragm, provided in the pump case so as to define a pump amber communicated with an external member having an air chamber; and
 an exhaust valve, comprising:
   a valve body, formed with a alit through which air in the pump chamber is exhausted; and
   a screw member, screwed into a first wall of the pump case to adjust an opening amount of the alit by a screwed amount thereof, thereby adjusting an exhausting rate of the air in the pump chamber,
 wherein the pump case is foamed with a ventilation hole communicated with the pump chamber to allow the air exhausted from the slit to pass through.

With this configuration, the pump case is formed with the ventilation hole which allows the air exhausted from the sit in the valve body to pass through, it is not necessary to provide such a ventilation hole in the screw member. Hence, it is possible to employ a low-cost screw member which has been generally used, as the screw member.

In addition, because the exhaust valve is provided inside the pump ease, it is possible to provide a compact pump in which the exhaust valve device and the pump device are integrated, having no exterior piping.

Preferably, the valve body is disposed between the first wall and a second wall of the pump case which opposes to the first wall. The screw member is abutted against the valve member to adjust a compressed state of the valve member between the screw member and the second wall.

With this configuration, the opening amount of the alit can be simply, quickly and accurately adjusted.

Preferably, the valve body is formed with an opening having a non-circular cross section including a first section opposing to the screw member and a second section not opposing to the screw member, but opposing to the ventilation hole.

With this configuration, since the second section opposes to the ventilation hole, the air exhausted from the slit can pass through the second region and the ventilation hole even when the screw member abuts against the first section of the valve body. That is, the air in the pump chamber can be exhausted irrespective of the shape of the screw member.

Preferably, the valve body is monolithically formed with the diaphragm.

With this configuration, it is possible to decrease the components in number, simplification, downsizing and decrease in weight of the structure.

According to the invention, there is also provided a hemodynamometer, comprising:
a cuff, adapted to be attached on a patient body and having an air chamber; and
a pump, comprising:
 a pump case;
 a diaphragm, provided in the pump case so as to define a pump chamber communicated with the air chamber; and
 an exhaust valve, comprising:
  a valve body, formed with a slit through which air in the pump chamber is exhaust; and
  a screw member, screwed into a first wall of the pump case to adjust an opening amount of the slit by a screwed amount thereof, thereby adjusting an exhausting rate of the air in the pump chamber,
wherein the pump case is formed with a ventilation hole communicated with the pump chamber to allow the air exhausted from the slit to pass through.

With this configuration, it is possible to obtain the hemodynamometer which is compact, lightweight and can be easily assembled

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

One preferred embodiment of the invention will be described below in detail with reference to the accompanying drawing In the following description, although there will be described a case where a compact pump is used with a hemodynamometer, the compact pump is not necessarily limited to the use with the hemodynamometer.

Figure 1:
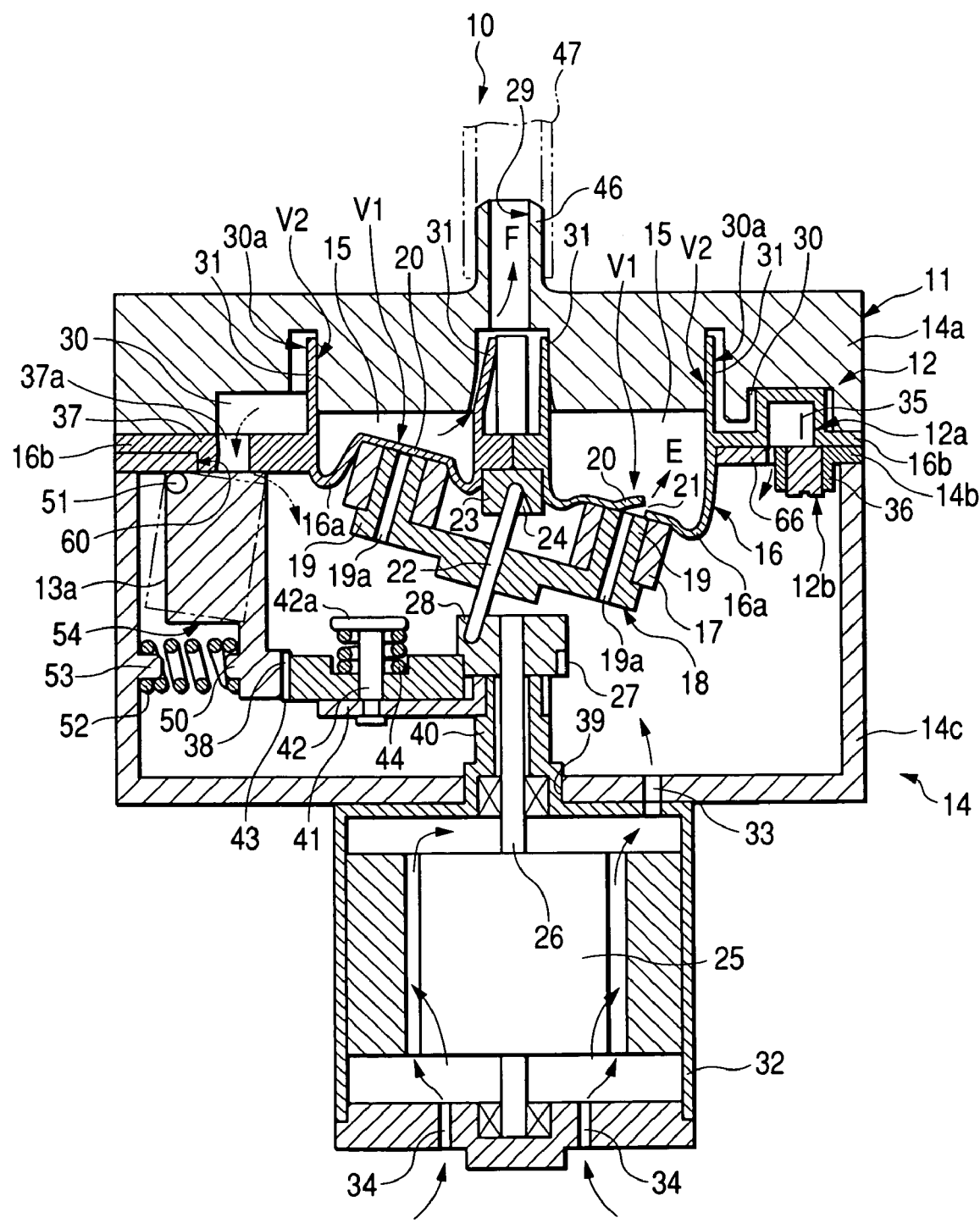
FIG. 1 is a vertical section view of a pump according to one embodiment of the invention.

As shown in FIG. 1, a compact pump 10 according to this embodiment is so constructed that a normal exhaust valve 12 and a rapid exhaust valve 13 are provided in a pump body 11.

The pump body 11 has a pump case 14 in a rectangular shape in a plan view, in which a diaphragm body 16 having two diaphragm parts 16a which define pump chambers 15 is provided. The diaphragm body 16 is formed of flexible material such as robber material or soft plastic material having elasticity. A hollowed mounting body 17 is attached on a lower face of each of the diaphragm parts 16a. A rocking body 18 for actuating the diaphragm parts 16a in the vertical direction is coupled with the lower face of the diaphragm parts 16a through the respective mounting bodies 17. The pump case 14 is composed of an upper case 14a, an intermediate case 14b and a lower case 14c. The diaphragm body 16 is held in the pump case 14 in a state where a flange portion 16b of the diaphragm body 16 is clamped between the upper case 14a and the intermediate 14b.

Projections 19 are formed in the vicinity of a periphery of the rocking body 18 so as to extend upward and fitted into the hollowed portion of the mounting bodies 17. Each of the projections 19 is formed with a through hole serving as an intake port 19a.

A center bottom part of each diaphragm part 16a is partly cut so as to form a valve body 20 and a through hole 21 which is opened or closed by the valve body 20 to constitute an intake valve V1.

A rotary shaft 22 for rocking the rocking body 18 by eccentric rotation is fittingly passed through a center part of the rocking body 18. An upper end of the rotary shaft 22 is fitted into a recess 24 formed in a protrusion 23 provided on the intermediate case 14 and above the rocking body 18. A lower end of the rotary shaft 22 is loosely fitted into a recess 28 which is eccentrically formed in a driving gear 27 coupled with a rotary shaft 26 of a motor 25. The motor 25 is disposed on a lower face of the lower case 14c.

A central part of an upper face of the upper case 14a is extended upward as a projection 46 formed with an exhaust port 29. A lower face of the upper case 14a is farmed with two annular grooves 30 each of which is communicated with the exhaust port 29. A valve body 31 formed as a part of each diaphragm part 16a is brought into press contact with an inner peripheral face 30a of each annular groove 30 to constitute an exhaust valve V2. The projection 46 is fitted into a flexible tube 47 so as to communicate the exhaust port 29 with a cuff (not shown).

A motor case 32 containing the motor 25 is connected to the lower case 14 such that inner spaces of the motor case 32 and the lower case 14c are communicated through a through hole 33. At least one intake port 34 for introducing exterior air is formed at a lower face of the motor case 32.

Figure 2:
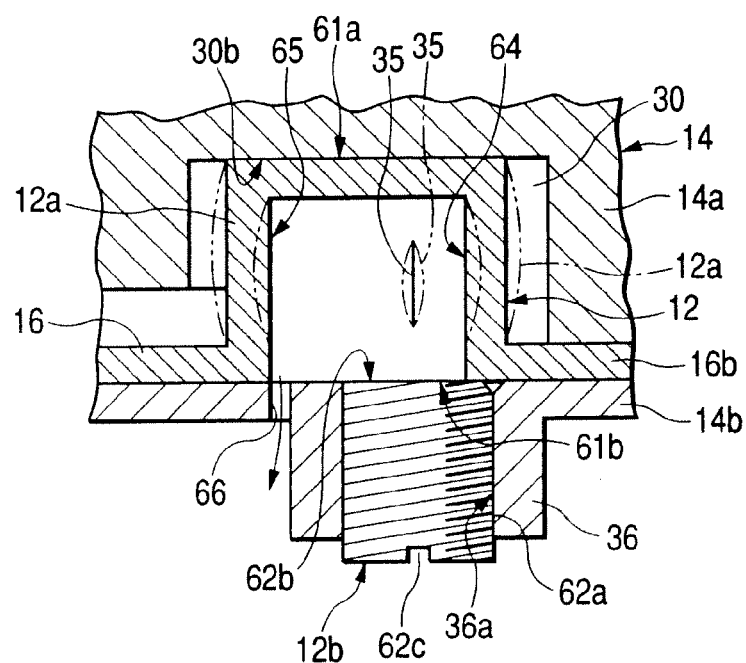
FIG. 2 is an Urged section view of a normal exhaust valve in the pup.
Figure 3:
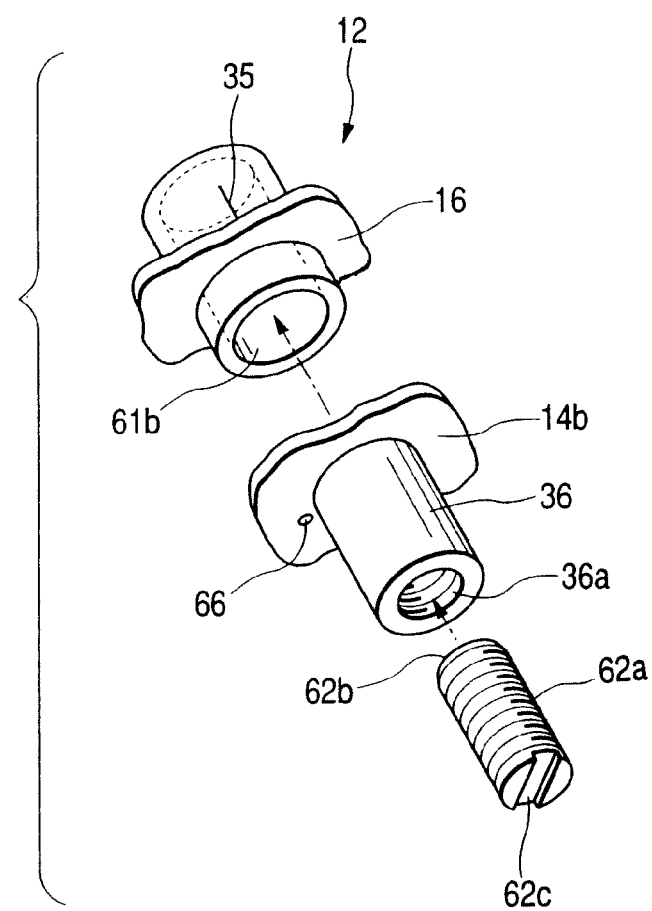
FIG. 3 is a perspective view of the normal exhaust valve in a disassembled state.

As shown in FIGS. 1 through 3, the normal exhaust valve 12 is provided so as to be associated with one of the annular grooves 30. The normal exhaust valve 12 comprises a valve body 12a formed as a part of the diaphragm body 16, and an adjuster screw 12b fitted into a tubular projection 36 formed on the intermediate case 14b for adjusting an exhausting rate of the valve body 12a.

Specifically, the valve body 12a is formed as a hollowed cylindrical projection and integrated with the diaphragm body 16. A closed upper end face 61a of the valve body 12a is brought into contact with a bottom face 30b of the annular groove 30. An actuating face 62b of the adjuster screw 12b is abutted against a part of a lower face of a periphery of a lower opening 61b of the valve body 12a. A slit 35 extending in the vertical direction is formed in a side periphery of the valve body 12a.

Figure 4:
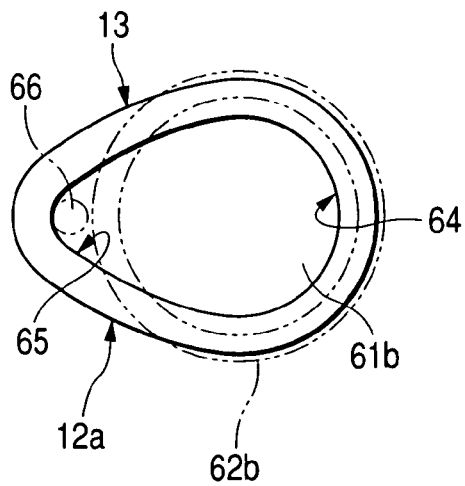
FIG. 4 is a schematic plan view of an essential part of the normal exhaust valve.

A shape of the lower opening 61b is not circular but oval as shown in FIG. 4. A dashed chain line in this figure represents the actuating face 62b of the adjuster screw 12b. The oval lower opting 61b has a first section 64 which is made smaller than the outer diameter of the actuating face 62b, and a second section 65 which is situated outside the actuating face 62b.

The intermediate case 14b is formed with a ventilation hole 66 so as to oppose to the second section 65 of the oval lower opening 61b of the valve body 12a That is, the interior of the valve body 12a is communicated with the interior of the pump case 14 through the ventilation hole 66.

A thread groove 62a is formed on an outer periphery of the adjuster screw 12b. An end face Opposite to the actuating face 62b is formed with a groove 62c. That is, the adjuster screw 12b may be provided as a screw body of general purpose type. On the other hand, an inner periphery of the tubular projection 36 is formed with a thread groove 36a, so that the adjuster screw 12b is screwed into the hollowed portion of the tubular projection 36. By fitting a distal end of a screwdriver into the groove 62c and rotating the adjuster screw 12b to the right, the adjuster screw 12b moves upward (i.e., toward the valve body 12a). To the contrary, by rotating to the left, the adjuster screw 12b moves downward (i.e., separating from the valve body 12a). In this embodiment, the screw body of general purpose type having no head is employed as the adjuster screw 12b. However, a screw body of general purpose type having a head such as a round headed screw and a dish headed screw may be also employed A solid line in FIG. 2 depicts a state that the actuating face 62b of the adjuster screw 12b is slightly abutted against the periphery of the lower opening 61b of the valve body 12a. Further rotating the adjuster screw 12b to the right from this state, the adjuster screw 12b moves toward the valve body 12a as described the above, so that the valve body 12a is compressed between the bottom face 30b of the annular groove 30 and the actuating face 62b. According to this compression, the valve body 12a is bulged and the slit 35 is opened as indicated by dashed chain lines in FIG. 2.

In this state, air in the annular groove 30 is exhausted to the interior of the pump case 14 through the slit 35, the second section 35 of the lower opening 61b and the ventilation hole 66. The opening degree of the slit 35 corresponding to the Off Red amount of the valve body 12a can be adjusted by the moving amount of the adjuster screw 12b. In other words, the exhaust rate of the air in the cuff (the lowering rate of the internal pressure in the cuff) can be controlled by the adjustment This adjustment is conducted in a course of assembling, but usually, will not be conducted after assembled, except in case of maintenance and inspection.

Figure 5:
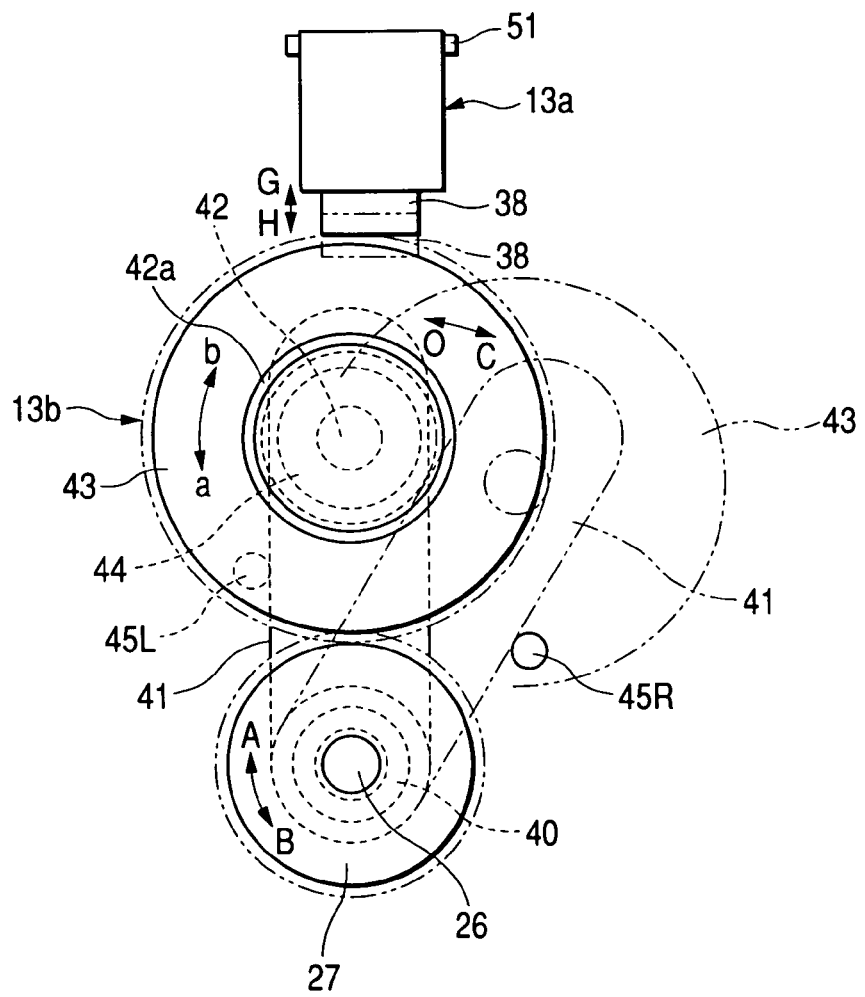
FIG. 5 is an enlarged plan view of a rapid exhaust valve in the pump.
Figure 6:
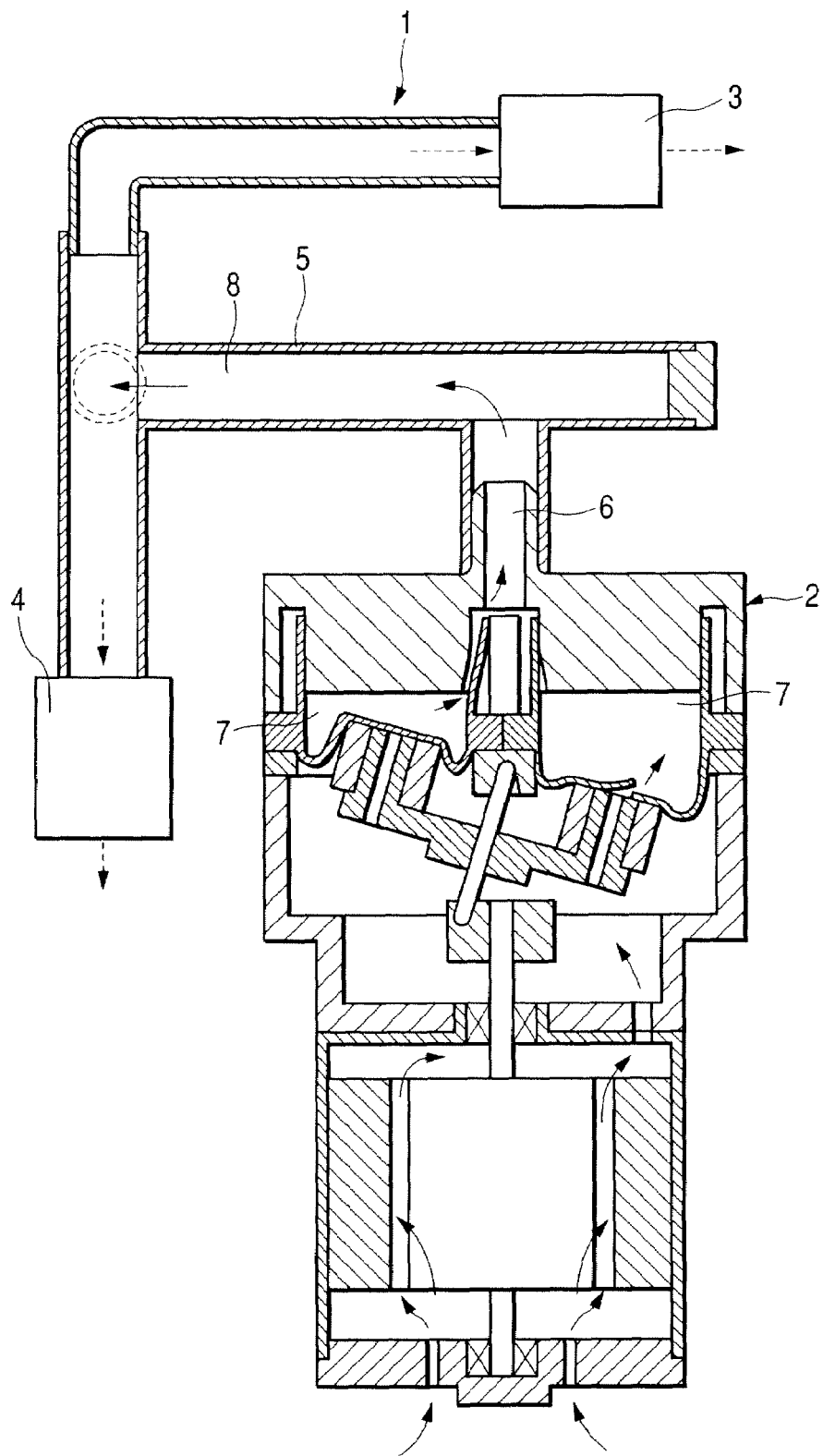
FIG. 6 is a vertical section view of a related-art pump.

As shown in FIGS. 1 and 5, the rapid exhaust valve 13 is provided so as to be associated with the other one of the annular grooves 30. The rapid exhaust valve 13 comprises: an exhaust section 37 formed with an exhaust port 37a at a center portion thereof, a valve body 13a which opens or closes the exhaust port 37a; and an actuator 13b which actuates the valve body 13a. The intermediate case 14b is formed with a cut out 60 for receiving the exhaust section 37 such that the exhaust port 37a is communicated with the interior of the pump case 14.

The valve body 13a is formed of resin in a rectangular pillar shape. A top face thereof is made flat and smooth. A recess 54 is formed at a lower portion of a first side face of the valve body 13a, and a projection 50 is formed in the recess 54 so as to extend toward the inner face of the lower case 14c. An engagement piece 38 is formed at a lower portion of a second side face of the valve body 13a which is opposite to the first side face. A hinge 51 is provided at a corner portion between the top face and the upper portion of the first side face.

Accordingly, the valve body 13a can be pivoted in the vertical direction about the hinge 51. When the valve body 13a is pivoted upward, the top face of the valve body 13a is abutted against the lower face of the exhaust section 37 so as to close the exhaust port 37a. When the valve body 13a is pivoted (inclined) downward, the top face of the valve body 13a is separated from the lower face of the exhaust section 37 so as to open the exhaust port 37a. The solid lines in FIG. 1 depict the position of the valve body 13a closing the exhaust port 37a (hereinafter, referred as "valve closing position"). The dashed chain lines in FIG. 1 depict the position of the valve body 13a opening the exhaust port 37a (hereinafter, referred as "valve opening position").

The inner face of the lower case 14c is formed with a projection 53 so as to oppose the projection 50 in the recess 54 of the valve body 13a. A coiled spring 52 is disposed between the valve body 13a and the lower case 14c in a compressed state One end of the coiled spring 52 is hooked on the projection 50, and the other end of the coiled spring 52 is hooked on the projection 53. Accordingly, the valve body 13a is always urged toward the valve closing position, so that the exhaust port 37a is closed in a usual state.

A beating portion 40 of the motor case 32 extends to the interior of the pump case 14 through a central through so hole 39 together with the rotary shaft 26 of the motor 25. As shown in FIG. 5, the valve actuator 13b comprises: a pivot lever 41 one end of which is attached on the bearing portion; a shaft member 42 provided on the other end of the pivot lever 41; a follower gear rotatably provided on the pivot lever through the shaft member 42; and a coiled clutch spring 44. The lower case 14c is formed with a pin-shaped stopper 45R for restricting the rightward pivot movement of the pivot lever 41 about the bearing portion 40, and a pin-shaped stopper 45L for restricting the leftward pivot movement of the pivot lever 41.

The follower gear 43 is meshed with the driving gear 27 coupled with the rotary shaft 26. When the driving gear 27 is rotated in accordance with the driving of the motor 25, the follower pear 43 is also rotated accordingly.

The coiled spring 44 is disposed between a head portion 42a of the shaft member 42 and the follower gear 43, so that the lower face of the follower gear 43 is brought into slight contact with the upper face of the pivot lever 41.

In accordance with the rotation of the motor 25 in the direction as indicated by an arrow "A" in FIG. 5, the follower gear 43 rotates in the direction as indicated by an arrow "a". Incidentally, since clutch friction due to the abutment of the coiled spring 44, is generated between the pivot lever 41 and the follower gear 43, the pivot lever 41 pivots about the bearing portion 40 in the direction as indicated by an arrow "C" until the pivot lever 41 is brought into contact with the stopper 45R. When the pivot movement of the pivot lever 41 is restricted by the stopper 45R, the frictional coupling between the follower gear 43 and the pivot lever 41 is canceled, so that only the follower gear 43 continues to rotate together with the driving gear 27.

To the contrary, in accordance with the rotation of the motor 25 in the direction as indicated by an arrow "B" in FIG. 5, the follower gear 43 rotates in de direction as indicated by an arrow "b". Incidentally, since clutch friction due to the abutment of the coiled spring 44 is generated between the pivot lever 41 and the follower gear 43, the pivot lever 41 pivots about the bearing portion 40 in the direction as indicated by an arrow "O" until the pivot lever 41 is brought into contact with the stopper 45L. When the pivot movement of the pivot lever 41 is restricted by the stopper 45L, the frictional coupling between the follower gear 43 and the pivot lever 41 is canceled, so that only the follower gear 43 continues to rotate together with the driving gear 27.

The engagement piece 38 is so configured as to mesh with the follower gear 43 when the pivot lever 41 is pivoted in the direction of the arrow "O" by a predetermined amount. In such a condition, the engagement piece 38 receives a force directed in the direction as indicated by an arrow "G" in FIG. 5 from the follower gear 43. The force in the direction "G" moves the valve body 13a so as to pivot about the hinge 51 downward (toward the valve opening position) against the urging force of the coiled spring 52.

That is, when the motor 25 is rotated in the direction "A" and the pivot lever 41 is abutted against the stopper 45R, the valve body 13a is placed at the valve closing position.

To the contrary, when the motor is rotated in the direction "B" and the pivot lever 41 is moved in the direction "O" by the predetermined amount, the follower gear 43 meshes with the engagement piece 38. In accordance with the further pivot of the pivot lever 41, the follower gear 43 pushes the engagement piece 38 in the direction "G" so that the valve body 13a opens the exhaust port 37a. As a result, the air in the annular grooves 30 (that is, the air in the cow is rapidly exhausted through the exhaust port 37a.

Next, the operation of the compact pump 10 configured as described the above will be described When the motor 25 is rotated in the direction "A" in FIG. 5, the rotary shaft 22 coupled through the rotary shaft 26 and the driving gear 27 is also rotated to rock the rocking body 18. The bottom parts of the diaphragm parts 16a in the diaphragm body 16 are vertically moved in accordance with the movement of the rocking body 18. For example, when one of the diaphragm parts 16a is moved downward, the interior pressure of the one diaphragm part 16a is made negative. Accordingly, the valve body 31 comes in dose contact with the inner peripheral face 30a of one annular groove 30 to close the exhaust valve V2. On the other hand, the valve body 20 opens the through hole 21 to open the intake valve V1, so that air is introduced into the one diaphragm part 16a from the intake port 19a as indicated by an arrow "E" in FIG. 1.

During the rotation of the motor 25 in the direction "A" in FIG. 5, the pivot lever 41 is moved to the stopper 45R and the follower gear 43 is separated from the valve body 13a of the rapid exhaust valve 13. Accordingly, the valve body 13a is pushed by the coiled spring 52 in a direction are indicated by an arrow "H" in FIG. 5, so that the valve body 13a is placed at the valve closing position of the rapid exhaust valve 13.

On the other hand, in accordance with the upward movement of the other one of the diaphragm parts 16a, the interior thereof is compressed. The valve body 20 accordingly doses the through hole 21 to bring the intake valve V1 in the closed condition. Incidentally, the valve body 31 is separated from the inner peripheral face 30a of the other annular groove 30 so that the exhaust valve V2 exhausts a as indicated by arrows "F" in FIG. 1. The exhausted air is supplied to the cuff (not shown) via the tube 47 coupled to the projection 46.

When the internal pressure of the cuff reaches a first predetermined value, the normal exhaust valve 12 is activated to exhaust air in the air passage. At the same time, larger amount of air than the above exhausted air is supplied to the cuff When the internal pressure of the cuff reaches a second predetermined value which is higher than the first predetermined value, tile motor 25 is halted, thereby halting the operation of the pump. Accordingly, the air in the air passage is exhausted by the normal exhaust valve 12 to gradually lower the internal pressure of the cuff. Incidentally, the internal pressure of the cuff and the vibration pattern due to the arterial pulsations are processed by the microcomputer to measure the systolic blood pressure and the diastolic blood pressure.

After the measurement processing, the motor 25 is rotated inversely (i.e., the direction "B" in FIG. 5), so that the pivot lever 41 is moved in the direction "O" in FIG. 5 together with the follower gear 43. The follower gear 43 is then meshed with the engagement piece 38 of the rapid exhaust valve 13, thereby pushing the engagement piece 38 in the direction "G" in FIG. 5. Accordingly, the valve body 13a is pivoted downward about the hinge 51, so that the exhaust port 37a of the exhaust part 37 is opened The air in the annular grooves 30 is exhausted from the exhaust port 37a, thereby rapidly exhausting the interior air of the cuff.

In the compact pump 10 of this embodiment, since the intermediate case 14b of the pump case 14 is formed with the ventilation hole 66 which allows the air exhausted from the slit 35 in the valve body 12a to pass through, it is not necessary to provide such a ventilation hole in the adjuster screw 12b. Hence, it is possible to employ a low-cost screw member which has been generally used, as the adjuster screw 12b.

Moreover, because the exhaust valve (the normal exhaust valve 12) is provided inside the pump case 14, it is possible to provide a compact pump in which the exhaust valve device and the pump device are integrated, having no exterior piping. In a case where the compact pump is assembled to another apparatus, for example, to a hemodynamometer, the pipes will not come into contact with other members and bent or crooked, which has made the assembling work difficult, will be eliminated. Therefore, the assembling work to another apparatus can be quickly and reliably conducted.

The valve body 12a can be deformed only by rotating se adjuster screw 12b, and the opening amount of the slit 35 can be Fly, quickly and accurately adjusted.

Since the diaphragm body 16 also serves as a part of the components composing the valve body 12a, it is possible to decrease the components in number, simplification, downsizing and decrease in weight of the structure.

In a case where the compact pump 10 having the above described structure is employed in the hemodynamometer, it is possible to obtain the hemodynamometer which is compact, light weight and can be easily assembled.

Although the description has been made referring to the case where the two diaphragm parts 16a are provided in the structure in this embodiment, the number of the diaphragm part 16a may be arbitrary.

Although the present invention has been &own and described with reference to special preferred embodiments, various changes and modifications will be apparent to those skilled in the art from the teachings her Such changes and modifications as are obvious are deemed to come within the spirit, scope and contemplation of the invention as Be in the appended claims.

What is claimed is:

1. A pump, comprising:
    a pump case composed of an upper case, an intermediate case and a lower case, a lower face of the upper case is formed with an annular groove which communicates with an exhaust port;
    a diaphragm body provided in the pump case between the upper case and the intermediate case so as to define a pump chamber communicated with an external member having an air chamber; and
    an exhaust valve, comprising:
        a valve body, formed as a hollowed cylindrical projection and integrated with diaphragm body and having a slit through which air in the pump chamber is exhausted, a closed upper end face of the valve body being brought into contact with a bottom face of the annular groove; and a solid adjuster screw, screwed into the intermediate pump case, an actuating face of the adjuster screw being abutted against a part of a lower face of a periphery of a lower opening of the valve body to deform the valve body to adjust an opening amount of the slit by a screwed amount of the adjuster screw, thereby adjusting an exhausting rate of the air in the pump chamber, wherein the lower opening of the valve body is oval in shape, a first portion of the lower opening being smaller than an outer diameter of the actuating face of the adjuster screw and a second portion of the lower opening situated outside the actuating face of the adjuster screw, the intermediate pump case being formed with a ventilation hole communicated with second portion of the lower opening and the pump chamber to allow the air exhausted from the slit to pass through.

2. A hemodynamometer, comprising:

a cuff, adapted to be attached on a patient body and having an air chamber; and a pump, comprising:

a pump case composed of an upper case, an intermediate case and a lower case, a lower face of the upper case is formed with an annular groove which communicates with an exhaust port;

a diaphragm body provided in the pump case between the upper case and the intermediate case so as to define a pump chamber communicated with an external member having an air chamber; and an exhaust valve, comprising:

a valve body, formed as a hollowed cylindrical projection and integrated with diaphragm body and having a slit through which air in the pump chamber is exhausted, a closed upper end face of the valve body being brought into contact with a bottom face of the annular groove; and a solid adjuster screw, screwed into the intermediate pump case, an actuating face of the adjuster screw being abutted against a part of a lower face of a periphery of a lower opening of the valve body to deform the valve body to adjust an opening amount of the slit by a screwed amount of the adjuster screw, thereby adjusting an exhausting rate of the air in the pump chamber, wherein the lower opening of the valve body is oval in shape, a first portion of the lower opening being smaller that an outer diameter of the actuating face of the adjuster screw and a second portion of the lower opening situated outside the actuating face of the adjuster screw, the intermediate pump case being formed with a ventilation hole communicated with second portion of the lower opening and the pump chamber to allow the air exhausted from the slit to pass through.

* * * * *